US005858964A

United States Patent [19]

Aharoni et al.

[11] Patent Number: 5,858,964
[45] Date of Patent: *Jan. 12, 1999

[54] PHARMACEUTICAL COMPOSITIONS COMPRISING SYNTHETIC PEPTIDE COPOLYMER FOR PREVENTION OF GVHD

[75] Inventors: Rina Aharoni; Ruth Arnon, both of Rehovot, Israel; Nelson J. Chao, Menlo Park, Calif.; Paul G. Schlegel, St. Georgen, Germany; Michael Sela; Dvora Teitelbaum, both of Rehovot, Israel

[73] Assignees: Yeda Research and Development Co. Ltd., Rehovot, Israel; Board of Trustees of the Leland Stanford Junior University, Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 540,388

[22] Filed: Oct. 6, 1995

Related U.S. Application Data

[63] Continuation-in-part of Ser. No. 421,412, Apr. 14, 1995, abandoned.

[51] Int. Cl.$^6$ ..................................................... A61K 31/74
[52] U.S. Cl. ........................................................ 514/2
[58] Field of Search ................................................ 514/2

[56] References Cited

U.S. PATENT DOCUMENTS 3,389,550  6/1968  Teitelbaum et al. .......................... 514/2

FOREIGN PATENT DOCUMENTS 9531990  11/1995  WIPO .

OTHER PUBLICATIONS

Aharoni et al., "T Suppressor Hybridomas and Interleukin–2–Dependent . . . ," *Eur. J. Immunol.*, vol. 23, 17–25, 1993.
Bornstein et al., "Clinical Trails of COP 1 in Multiple Sclerosis," Marcel Dekker, Chapter 22, pp. 469–480 1995.
Fridkis–Hareli et al., "Direct Binding of Myelin Basic Protein and Synthetic . . . ," *Proc. Natl. Acad. Sci.*, vol. 91, pp. 4872–4876, May 1994.c.o.
Jacob et al., "DNA Polymorphism in Cytokine Genes Based on Length . . . ," *Immunogenetics*, vol. 38, pp. 251–257, 1993.
Johnson, K., "Copolymer I; Positive Results From A Phase III Trial . . . ", American Neurological Association, 200 word abstract, date is not available.
Schlegel et al., "Inhibition of Allorecognition and Prevention of Graft–vs–Host Disease (GVHD) By GLAT, a Synthetic Polymer with Promiscuous Binding to Murine and Human MHC Class II Molecules," 37th Annual Meeting of the America Society of Hematology, Seatle, Washington, Dec. 1–5, 1995, *Blood* 86 (10 Suppl. 1) 1995 224A, XP00578001.
Schlegel et al., "Prevention of Graft–vs–Host Disease by Peptides Bonding . . . ," *Blood*, vol. 84, No. 8, pp. 2802–2810, Oct. 15, 1994.
SELA et al., "Suppressive Activity of COP–1 in EAE . . . ," *Bull. Inst. Patuer.*, vol. 88, pp. 303–314, 1990.
Teitelbaum et al., "Suppression of Experimental Allergic Encephalomyelitis . . . ," *Eur. J. Immunol.*, vol. 1, pp. 242–248, 1971.
Teitelbaum et al., "Suppression by Several Synthetic Polypetides . . . ," *Eur. J. Immunol.*, vol. 3, pp. 273–279, 1973.
Teitelbaum et al., "Suppression of Experimental Allergic Encephalomyclitis . . . ," *Clinical Immunology and Immunopathology*, vol. 3, pp. 256–262, 1974.
Teitelbaum et al., "Suppression of Experimental Allergice Encephalomyelitis . . . ," *Israel J. Med. Sci.*, vol. 13, pp. 1038, 1977.
Teitelbaum et al., "Specific Inhibition of the T–Cell Response . . . ," *Proc. Natl. Acad. Sci.*, vol. 85, pp. 9724–9728, Dec. 1988.
Teitelbaum et al., "Molecular Requirements Involved in Suppression . . . ," *Immunochemistry*, vol. 13, pp. 333–337, 1976.

*Primary Examiner*—Cecilia J. Tsang
*Assistant Examiner*—Patrick R. Delaney
*Attorney, Agent, or Firm*—Browdy and Neimark

[57] ABSTRACT

Pharmaceutical compositions comprising as active ingredient a synthetic random copolymer of average molecular weight of about 4,000–12,000, preferably 6,000–8,000, said copolymer consisting of glutamic acid (Glu), lysine (Lys), alanine (Ala) and tyrosine (Tyr) residues in a relative molar ratio of 1.4–2.1 parts of Glu to 3.2–4.4 parts of Lys to 4.0–6.0 parts of Ala to 1.0 parts of Tyr (herein GLAT copolymers), can be used in a method for prevention and treatment of graft-versus-host disease in patients in the course of bone marrow and organ transplantation.

16 Claims, 3 Drawing Sheets

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( D ) OTHER INFORMATION: The alanine at position 1 is acetylated ( x i ) SEQUENCE DESCRIPTION: SEQ ID NO:1:

Ala Ser Gln Ala Arg Pro Ser Gln Arg His Gly
1               5                   10

( 2 ) INFORMATION FOR SEQ ID NO:2:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Thr Gly Ile Leu Asp Ser Ile Gly Arg Phe Phe Ser Gly
1               5                   10

( 2 ) INFORMATION FOR SEQ ID NO:3:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Lys Met Lys Met Val His Ala Ala His Ala Lys Met Lys Met
1               5                   10

( 2 ) INFORMATION FOR SEQ ID NO:4:

```
( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Val   His   Phe   Phe   Lys   Asn   Ile   Val   Thr   Pro   Arg   Thr   Pro
    1                       5                             10

( 2 ) INFORMATION FOR SEQ ID NO:5:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:5:

CCAAGCTTCC TTGTGCAAGT A                                                    2 1

( 2 ) INFORMATION FOR SEQ ID NO:6:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:6:

AGCCCAAAGT CCATCAGTGG                                                      2 0
```

PHARMACEUTICAL COMPOSITIONS COMPRISING SYNTHETIC PEPTIDE COPOLYMER FOR PREVENTION OF GVHD

CROSS REFERENCE TO RELATED APPLICATION

The present application is a continuation-in-part of U.S. application Ser. No. 08/421,412, filed Apr. 14, 1995 now abandoned, the entire contents of which are hereby incorporated herein by reference.

FIELD OF THE INVENTION

The present invention relates to organ transplantation in humans in general, and more specifically to prevention of graft-versus-host-disease, particularly in bone marrow transplantation.

BACKGROUND OF THE INVENTION

Bone marrow transplantation (BMT) is increasingly used in humans for treatment of many life-threatening hematologic disorders, especially leukemia and certain immune deficiency diseases. However, graft-versus-host disease (GVHD) remains the major barrier for effective allogeneic bone marrow transplantation. This complication occurs in approximately 30% of bone marrow recipients. Up to half of those patients who develop GVHD may succumb to this process. This high morbidity and mortality has led to continuous interest in the possibility of controlling or preventing GVHD.

Current available approaches for prevention of GVHD include the use of non-specific immunosuppressive drugs, such as cyclosporine, methotrexate and/or prednisone. However, this treatment induces severe side effects, including nephrotoxicity, hypertension, hypercholesterolemia, diabetogenic effects, neurotoxicity, hirsutism and gengival hyperplasia. Moreover, the unselective depression of the entire immune system renders patients vulnerable to infections. In addition to the chronic administration of toxic, immunosuppressive agents, successful human allogeneic bone marrow transplantation depends, at the moment, on the availability of a suitable histocompatibility donor.

Clinicopathologically, two forms of GVHD have been recognized. Acute GVHD develops within the first 3 months after BMT and features disorders of skin, liver and gastrointestinal tract. Chronic GVHD is a multiorgan autoimmune-like disease, emerging from 3-month up to 3 years post-transplantation and shares features common to naturally occurring autoimmune disorders, like systemic lupus erythematosus (SLE) and scleroderma.

GVHD is caused by the competent donor T cells reacting against minor histocompatibility antigens of the recipient. The donor T cells are sensitized to such alloantigens and then directly, or through secondary signals, attack the host cells.

One approach for prevention of GVHD in murine models was recenty described by the inventors (Schlegel et al., 1994). The data reported therein show for the first time that GVHD can be prevented by administration of small peptides with high affinity for class II MHC molecules, and that the mechanism of prevention is MHC-associated. The precise mechanism of how these peptides prevent GVHD has still to be determined. However, the treatment with blocking peptides is limited by the specificity of the tested peptide to specific murine (or human) haplotype. Other disadvantages of using small peptides is the rapid clearance and the relatively short binding half-life to the MHC molecule.

The present invention relates to the use of a synthetic random copolymer consisting of glutamic acid (Glu), lysine (Lys), alanine (Ala) and tyrosine (Tyr) residues, in a relative molar ratio of 1.4–2.1 parts of Glu, 3.2–4.2 parts of Lys, and 4.0–6.0 parts of Ala to 1 part Tyr, with average molecular weight of 4,000–12,000, herein referred to as GLAT copolymer. The Glu, Lys, Ala and Tyr residues in the GLAT copolymer may all have the L (L-GLAT) or the D (D-GLAT) configuration, or some of the amino acid residues will have A high molecular weight synthetic basic random copolymer consisting of L-Ala, L-Glu, L-Lys and L-Tyr residues in the molar ratio of about 6 parts Ala to 2 parts Glu to 4.5 parts Lys to 1 part Tyr, and having a molecular weight of 15,000–25,000, was first described in U.S. Pat. No. 3,849,550 as an agent for treatment or prevention of experimental allergic encephalomyelitis (EAE), a disease resembling multiple sclerosis (MS) that can be induced in susceptible animals. Batches of this copolymer of average molecular weight 23,000, designated Copolymer 1 or Cop 1, were shown to be highly effective in protecting and suppressing EAE in several animal species (Teitelbaum et al., 1971, 1974a, 1974b). Later, Cop 1 was found to significantly reduce the number of relapses in patients with the exacerbating-remitting form of MS (Bornstein et al., 1990; Sela et al., 1990; Johnson et al., 1994).

The mechanism underlying the therapeutic activity of Cop 1 in MS has been extensively studied. Cop 1 was found to be immunologically cross-reactive with myelin basic protein (MBP), the main autoantigen in EAE and MS. Its suppressive effect results from several mechanisms, such as inhibition of the autoreactive pathogenic T-cells on one hand (Teitelbaum et al., 1988), and stimulation of suppressor cells on the other hand (Aharoni et al., 1993). The first step essential for the activation of these specific processes is the binding of Cop 1 to the histo-compatibility molecules. Indeed, it has been shown that Cop 1-two different batches of molecular weight 5,550 and 8,600, and relative molar ratio of L-Ala (4.1–5.8 residues), L-Glu (1.4–1.8 residues), L-Lys (3.2–4.2 residues) and L-Tyr (1 residue)—binds very efficiently to a variety of MHC class II molecules of mouse and human origin, and furthermore competes with MBP and its major epitope p84–102 for MHC binding and can even displace such antigens that had already been bound to the MHC molecule (Fridkis-Hareli et al., 1994).

None of the prior art publications describes or suggests that Cop 1 may be used to prevent or to treat GVHD.

SUMMARY OF THE INVENTION

It has now been found in accordance with the present invention that a GLAT copolymer can be used successfully to prevent experimental graft-versus-host disease by applying an animal model which is similar to the matched bone marrow transplantation in humans. This murine system comprises of bone marrow and spleen cells of B10.D2 mice transplanted to BALB/c recipients (both H-$2^d$), but clearly different in minor histocompatibility antigens.

The present invention thus relates, in one aspect, to a pharmaceutical composition for use in the prevention and treatment of graft-versus-host disease comprising as active ingredient a synthetic random copolymer of average molecular weight of about 4,000–12,000 consisting of glutamic acid, lysine, alanine and tyrosine residues, in a relative molar ratio of 1.4–2.1 parts of Glu to 3.2–4.2 parts of Lys to 4.0–6.0 parts of Ala to 1.0 part of Tyr, herein referred to as GLAT copolymer, together with physiologically acceptable carriers.

The GLAT copolymer used in the present invention has preferably an average molecular weight of about 5,500–10,000 Da, more preferably of 6,000–8,000 Da, and most preferably, of about 6,000 or of about 8,000.

The Glu, Lys, Ala and Tyr residues may all have the L-configuration (L-GLAT) or the D configuration (D-GLAT) or some of the residues have the L, and the others the D, configuration (DL-GLAT). In one preferred embodiment, L-GLAT is used in the invention.

Preferred molar ratios of the amino acid residues include the relative molar ratios 1.7 Glu to 3.8 Lys to 4.9 Ala to 1.0 Tyr, and 1.9 Glu to 4.0 Lys to 6.0 Ala to 1 Tyr.

Although we have described above some preferred embodiments of the invention, it is to be understood that the present invention encompasses any synthetic random copolymer of Glu, Lys, Ala and Tyr, having a relative molar ratio of the amino acid residues and an average molecular weight as defined herein, including those forms of Cop 1 described in the literature that fall within the definition of the present invention.

In another aspect the invention relates to the use of said GLAT copolymer for the manufacture of a medicament for prevention and treatment of graft-versus-host disease.

In a further embodiment the invention relates to a method of treatment of a patient for prevention and treatment of graft-versus-host disease in the course of bone marrow and organ transplantation, said method comprising administering to said patient effective amounts of said GLAT copolymer.

In a preferred embodiment, the GLAT copolymer is used according to the invention for prevention of graft-versus-host disease in allogeneic bone marrow transplantation, optionally together with other immunosuppressive agents.

DETAILED DESCRIPTION OF THE INVENTION

Figure 1A:
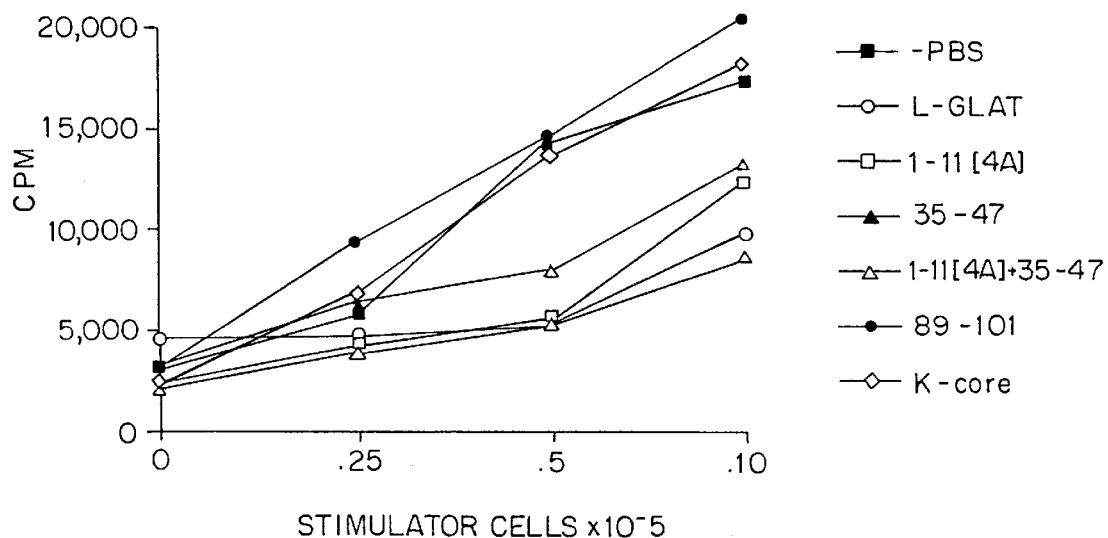
FIGS. 1A–B show the inhibition of secondary mixed lymphocyte reaction (MLR) across minor as well as major histocompatibility barriers, caused by several peptides. The peptides L-GLAT, MBP Ac1–11[4A], MBP 35–47, a mixture of MBP Ac1–11[4A]+MBP 35–47, MBP 89–101 and KM-core (all described in Materials and Methods hereinafter) were tested for their ability to inhibit the proliferation of B10.PL (H-2$^u$) mice responder cells to stimulator cells of either the same haplotype (PL/J mice, FIG. 1A) or of a different H-2 haplotype (BALB/c mice, FIG. 1B).

The GLAT copolymers used in the present invention represent a novel therapeutic approach to treat human graft-versus-host disease for effective organ, particularly bone marrow, transplantation.

The L-GLAT to be used according to the present invention may be prepared by methods known in the art, for example, the process disclosed in U.S. Pat. No. 3,849,550 and in Teitelbaum et al., 1971, wherein the N-carboxyanhydrides of tyrosine, alanine, γ-benzyl glutamate and ε-N-trifluoroacetyllysine are polymerized at ambient temperature in anhydrous dioxane with diethylamine as initiator, followed by deblocking of the γ-carboxyl group of the glutamic acid with hydrogen bromide in glacial acetic acid, and removal of the trifluoroacetyl groups from the lysine residues by 1M piperidine. L-GLAT with the required molecular weight profile of 4,000–12,000, preferably 6,000–8,000, can be obtained by methods known per se, for example, by chromatography of L-GLAT-containing high molecular weight species or by partial acid or enzymatic hydrolysis to remove the high molecular weight species with subsequent purification by dialysis or ultrafiltration.

D-Cop 1, an example of D-GLAT copolymer, has been found as non cross-reactive with either the L-copolymer, Cop 1, or with the natural autoantigen myelin basic protein, and failed to exhibit any suppressive activity on EAE, indicating that it does not have a therapeutic value relevant to MS (Webb et al., 1976). According to the present invention, it was found that D-GLAT binds as efficiently as L-GLAT to the MHC molecules, indicating that it may be useful for prevention and treatment of GVHD.

D-GLAT and DL-GLAT copolymers may be prepared similarly to L-GLAT copolymers using D and D+L carboxyanhydrides, respectively, of the corresponding amino acids. An advantage in using a D-GLAT or DL-GLAT copolymer resides in the fact that such polymers metabolize much slower than the L-isomer, and thus a longer half-life and higher concentrations of the effective material can be achieved.

The pharmaceutical compositions of the present invention comprising a GLAT copolymer are prepared by conventional methods known in the art. Preferably, the composition is lyophilized and formed into an aqueous solution suitable for subcutaneous, intramuscular or intravenous injection. Typically, a pharmaceutical composition will comprise from 10 to 100 mg of L-GLAT in an unit dose. D-GLAT and DL-GLAT copolymers may be used in lower doses.

The GLAT copolymer may be used according to the invention for prevention and treatment of GVHD in all cases of organ transplantation that develop GVHD, but particularly in fetal thymus, and more particularly, in allogeneic bone marrow, transplantation. To a patient under suitable conditioning regimen, the GLAT copolymer is administered from day −2 prior to the transplantation day, and then for another 60–100, at least 60, days, after the transplantation day. Other immunosuppressive drugs, such as cyclosporine, methotrexate and prednisone, may be administered with the GLAT copolymer.

The method of the invention is suitable for the prevention and treatment of GVHD in the course of bone marrow transplantation in patients suffering from diseases curable by bone marrow transplantation, including leukemias, such as acute lymphoblastic leukemia (ALL), acute nonlymphoblastic leukemia (ANLL), acute myelocytic leukemia (AML) and chronic myelocytic leukemia (CML), severe combined immunodeficiency syndromes (SCID), osteopetrosis, aplastic anemia, Gaucher's disease, thalassemia and other congenital or genetically-determined hematopoietic or metabolic abnormalities.

The invention will now be illustrated by the following non-limiting examples.

EXAMPLES

Materials and Methods (a) Preparation of GLAT copolymers and controls (i) L-GLAT was prepared by polymerization of the N-carboxyanhydrides of L-Ala, γ-benzyl-L-Glu, N,ε-trifluoroacetyl-L-Lys, and L-Tyr. The polymerization reaction was carried out at room temperature in anhydrous dioxane with diethylamine as initiator. Deblocking of the γ-carboxyl groups of the glutamic acid was carried out with hydrogen bromide in glacial acetic acid for 24 hours at room temperature, followed by removal of the trifluoroacetyl groups from the lysine residue by 1M piperidine. The end product is a mixture of acetate salts of random polypeptides with amino acid composition of Ala (4.1–5.8 residues), Glu (1.4–1.8 residues), Lys (3.2–4.2 residues), Tyr (1 residue). Two L-GLAT batches were used in the experiments: Batch I consisting of a copolymer of molecular weight of about 6,000, with the amino acids in the molar ratio of about 1.7 Glu to 3.8 Lys to 4.9 Ala to 1.0 Tyr, and Batch II, consisting of a copolymer of molecular weight of about 8,000, with the amino acids in the molar ratio of 1.8 Glu to 4.0 Lys to 6.0 Lys to to 1.0 Tyr.

(ii) D-GLAT was prepared by polymerization of the N-carboxyanhydrides of the D-amino acids D-Ala, γ-benzyl-D-Glu, N,ε-trifluoroacetyl-D-Lys, and D-Tyr in a residue molar ratio of 5.6:2.2:4.6:1.0 with an average molecular weight of approx. 29,000.

(iii) TGA is a random basic polymer of L-Tyr, γ-benzyl-L-Glu, and L-Ala in a residue molar ratio of 1.0:1.2:1.1. It was used as a negative control.

(iv) Hen egg-white lysozyme (HEL) was obtained from Sigma Chemical Company (St. Louis, Mo.).

(v) Peptides were synthesized by standard FMOC chemistry. All peptides were 95% to 99% pure, as determined by high-performance liquid chromatography, and were checked by amino acid analysis and mass spectroscopy. Sequences are given in three letter codes:

MBP Ac1–11[4A], an acetylated N-terminal 1–11 peptide of myelin basic protein (MBP), with substitution of the original Lys residue at position 4 by Ala: Ac-Ala-Ser-Gln-Ali-Arg-Pro-Ser-Gln-Arg-His-Gly (SEQ ID NO:1);

MBP 35–47, the epitope of MBP which is recognized in association with I-E$^u$: Thr-Gly-Ile-Leu-Asp-Ser-Ile-Gly-Arg-Phe-Phe-Ser-Gly (SEQ ID NO:2);

KM-core extension peptide, based on the antigenic core sequence of ovalbumin 323–339: Lys-Met-Lys-Met-Val-His-Ala-Ala-His-Ala-Lys-Met-Lys-Mel (SEQ ID NO:3);

MBP 89–101: Val-His-Phe-Phe-Lys-Asn-Ile-Val-Thr-Pro-Arg-Thr-Pro (SEQ ID NO:4). was synthesized by t-butoxy-carbonyl chemistry.

(b) Animals

B10.D2/nSnJ (H-2$^d$), B10.PL and PL/J (H-2$^u$) mice were purchased from The Jackson Laboratories (Bar Harbor, Me.); BALB/c (H-2$^d$) recipient mice were obtained from Simonsen Laboratories (Gilroy, Calif.).

(c) Mixed lymphocyte reaction (MRL)

Responder spleen cells were harvested from B10.PL (H-2$^u$) mice 21 days after prior immunization with irradiated (3,000R) 50×10$^6$ spleen cells from PL/J (H-2$^u$) mice. Responder cells (5×10$^5$ spleen cells/well) were tested for their proliferative response by plating with different amounts (2.5 to 10×10$^5$) of irradiated PL/J or BALB/c stimulator cells, in presence or absence of various peptide inhibitors (20 μg/well). Cultures were set up in 200 μl media containing 10% FCS in flat-bottom microtiter plates. After 4 days of incubation, cultures were pulsed with 1 μci of [$^3$H]-thymidine for an additional 16 hrs. Results are represented as mean counts per minute (cpm) thymidine incorporation from triplicate cultures.

(d) Assessment of GVHD

Mice were followed up daily for 140 days after bone marrow transplantation for signs of GVHD. Disease severity was assessed by mortality, loss of body weight, and by the extent of macroscopic skin involvement scored on a cumulative scale (from min 0–max 8): head 1, neck 1, back (1/3, 2/3, 3/3) 1–3, front (1/3, 2/3, 3/3) 1–3. Skin biopsies were examined as previously described (Schlegel et al., 1994).

(e) PCR analvsis

Engraftment of donor bone marrow was documented by PCR amplification of a polymorphic microsatellite region within the murine IL-1b gene. Primer sequences are as follows: 5'-CCAAGCTTCCTTGTGCAAGTA-3' (SEQ ID NO:5) and 5'-AAGCCCAAAGTCCATCAGTGG-3' (SEQ ID NO:6) (Jacob et al., 1993). These sequences are available from EMBL/Gen-Bank/DDBJ database (Bethesda, Md.) under the accession numbers: X78456 and X78457. Oligonucleotides were synthesized on a 391 DNA synthesizer (Applied Biosystems, Foster City, Calif.) and were purified. DNA was prepared from peripheral blood mononuclear cells 80–120 days after transplantation according to standard protocols. PCR conditions and amplification were as described previously (Schlegel et al., 1994).

Example 1

Inhibition of mixed lymphocyte reaction by L-GLAT

Mixed lymphocyte reaction (MLR), the proliferative response of allogeneic lymphocytes when cultured together, is considered an in vitro model for the recognition phase of the GVHD reaction, and is part of the routine screening for bone marrow donors.

To investigate the feasibility of inhibition of MLR by L-GLAT, an MLR system was developed in which L-GLAT was tested for its ability to inhibit the proliferation of B10.PL (H-2$^u$) responder cells to stimulator cells of either the same (PL/J) or different (BALB/c) H-2 haplotype. For comparison, the inhibitory MBP Ac 1–11[4A], MBP 35–47, a combination of Ac 1–11 [4A]+MBP 35–47, MBP 89–101 and KM-core peptides, described in Schlegel et al., 1994, were used in the MLR experiments.

Figure 1B:
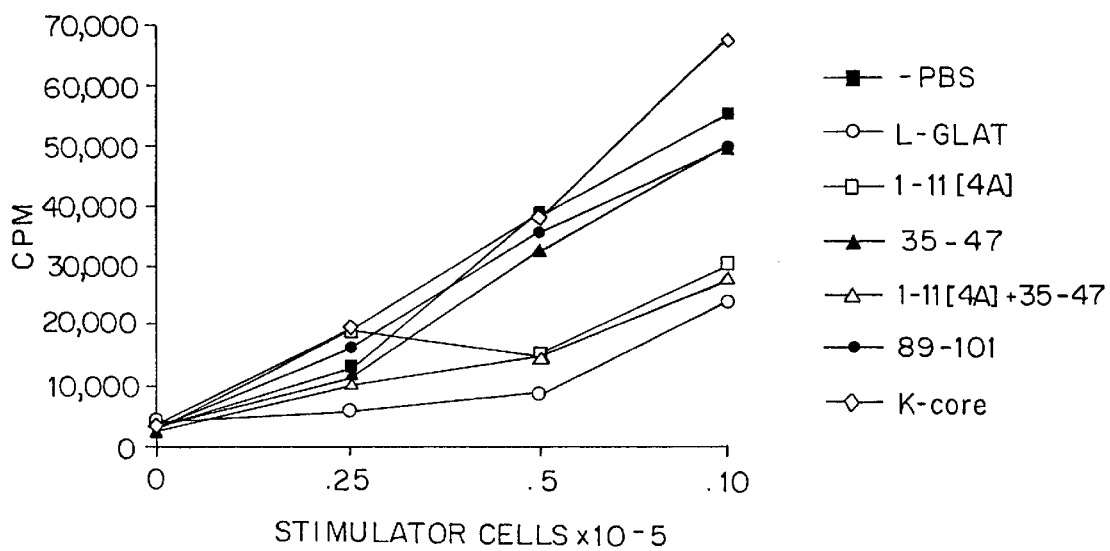

As shown in FIG. 1A for stimulator cells of PL/J mice and in FIG. 1B for stimulator cells of BALB/c mice, L-GLAT (Batch I) significantly inhibited MLR across minor as well as major histocompatibility barriers. 63% and 77% inhibition could be obtained, respectively, when 1:1 ratio of responder to stimulator cells was used, while the MBP 89–101 and the KM-core peptides, which are specific to the H-2$^s$ haplotype, did not induce any significant effect. The inhibition obtained by L-GLAT was similar (in response to minor histocompatibility antigen) or even higher (in response to major histocompatibility antigen) than the inhibition obtained with the combination of the two synthetic peptides Ac 1–11[4A] and MBP 35–47, which specifically bind to the class II molecules I-A$^u$ and the I-E$^u$, respectively. The molar efficiency of L-GLAT of M.W. 6000 is even higher since the molecular weight of the synthetic peptides is 4–5 fold lower.

Example 2

Bone marrow transplantation in mice, induction of GVHD and treatment with L-GLAT (i) Initial titration study. For the induction of GVHD across minor histocompatibility barriers, an initial titration study was performed by transplanting 10×10$^6$ B10.D2 bone marrow cells and increasing amounts (10–100×10$^6$) of B10.D2 spleen cells into lethally irradiated (8.0 Gy) 12–13 week old BALB/c recipients. The regimen of infusing $10 \times 10^6$ bone marrow cells and $100 \times 10^6$ spleen cells resulted in the most severe form of GVHD, and was selected for all subsequent experiments.

(ii) Effect of L-GLAT treatment on the incidence, onset and severity of GVHD. Recipient mice were treated with 600 μg of L-GLAT (Batch I) or control peptides or saline (PBS), half dose injected subcutaneously and half dose intraperitoneally, daily for the first five weeks after bone marrow transplantation, followed by a tapering schedule over an additional four weeks. All treatment was discontinued after 9 weeks.

The results are shown in Table 1. Treatment with L-GLAT (Batch I) significantly reduced the overall incidence of GVHD after allogeneic bone marrow transplantation: from 100% (10 of 10 or 6 of 6) in control mice to 0% (0 out of 10) in L-GLAT-treated animals on day 30 ($p<0.001$), and from 100% in controls to 2 out of 10 (20%) on day 70 after transplantation ($p<0.01$) In 4 out of 10 animals treated with L-GLAT, the onset of GVHD was delayed with a range of 54–79 days after transplantation (median onset of 69 days) as compared to PBS-controlled mice where the median onset was 21 days or control peptide HEL-treated mice, where the median onset was also again 21 days. Six out of the ten animals treated with L-GLAT did not develop any signs of GVHD beyond the observation period of 140 days after transplantation. Furthermore, treatment with L-GLAT improved overall disease severity as gauged by the mean disease severity score.

Similar results were obtained with Batch II of L-GLAT as shown in Table 2.

(iii) Effect of L-GLAT treatment on survival. Recipient BALB/c recipient mice were lethally irradiated (8Gy) and transplanted with $10 \times 10^6$ B10.D2 bone marrow and $100 \times 10^6$ B10.D2 spleen cells on day 0. Recipient mice were injected half dosage subcutaneously and half dosage intraperitoneally, with 600 μg L-GLAT (Batch I), HEL or PBS (FIG. 2A) or with L-GLAT (Batch II), TGA, HEL or PBS (FIG. 2B), daily for the first five weeks, followed by a tapering schedule over an additional four week period. All treatment was discontinued after nine weeks.

Figure 2A:
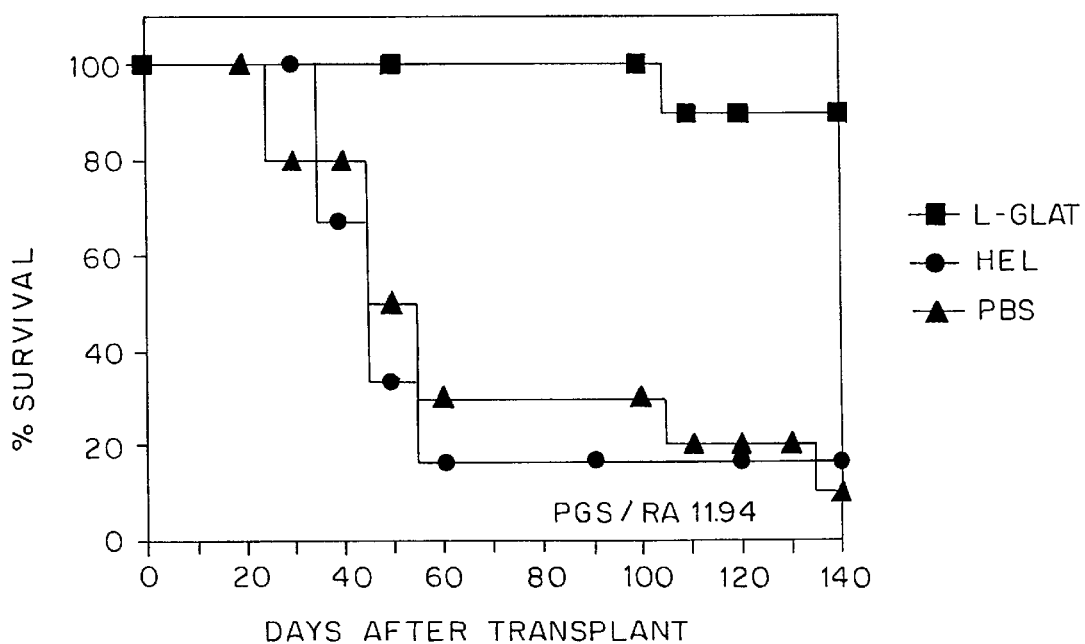
FIGS. 2A–B show the effect on survival of BALB/c mice transplanted with bone marrow and spleen cells from B10.D2 mice after treatment with L-GLAT, chicken egg lysozyme (HEL) or phosphate-buffered saline (PBS) (FIG. 2A) or with L-GLAT, HEL, PBS or TGA polymer (FIG. 2B).
Figure 2B:
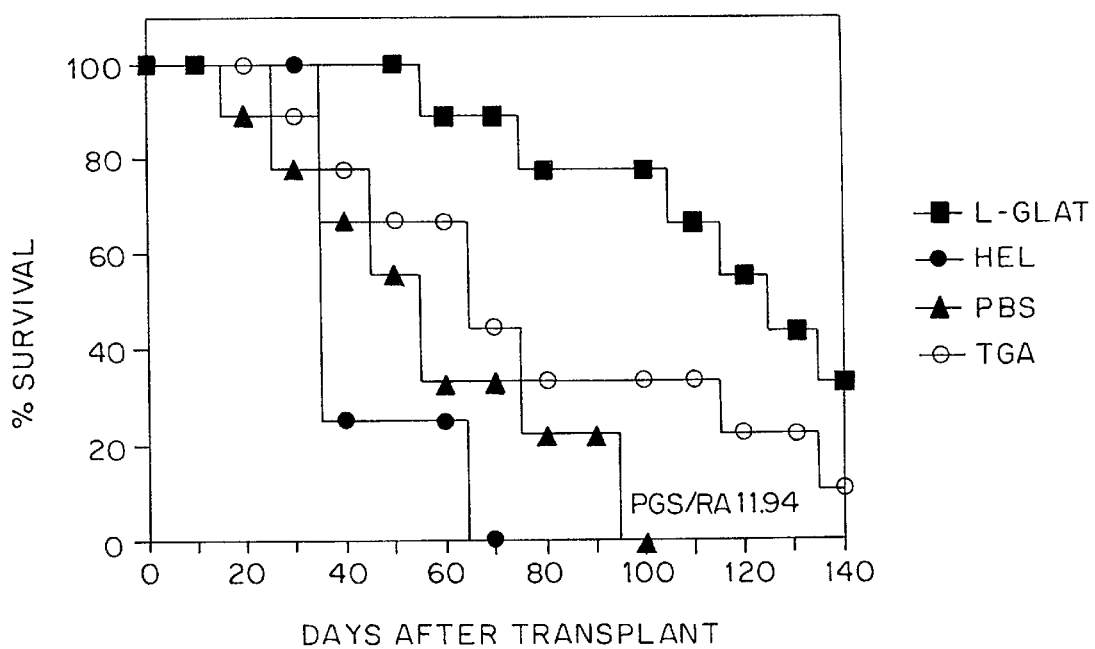

As shown in FIGS. 2A–B, treatment with L-GLAT for the first nine weeks after bone marrow transplantation improved long-term survival from lethal GVHD. FIG. 2A shows that 9 out of 10 (90%) experimental mice survived more than 140 days after transplant as compared to only 1 out of 10 for the PBS control or 1 out of 6 for the HEL-treated control mice. In these figures, means are ststed as overall means of the respective groups. GVHD-related mortality. MST: median survival time (in days). Statistical analysis: Incidence of GVHD by $x^2$ distribution: Experiment 1 (FIG. 2A): * $p<0.01$, ** $p<0.001$, L-GLAT compared to PBS or HEL-.Experiment 2 (FIG. 2B): $\pi p<0.02$, L-GLAT compared to PBS, TGA or HEL.

Similar results were obtained with L-GLAT Batch II, as shown in FIG. 2B.

(iv) Documentation of engraftment. PCR analysis was performed 100 days post-transplant as described in Materials and Methods, section e, to document long-term engraftment of allogeneic bone marrow cells. DNA polymorphism based on length variation in tandem repeat sequences of a microsatellite in the murine IL-1β gene was used as marker to differentiate between donor-derived (B10.D2/nSnJ) and recipient (BALB/c) peripheral blood mononuclear cells. Long-term engraftment of donor-derived cells was demonstrated in allogeneic mice by PCR analysis irrespective of the treatment received.

Example 3

Bone marrow transplantation in mice, induction of GVHD and treatment with D-GLAT (i) Initial titration study was carried out as in Example 2(i).

(ii) Effect of D-GLAT treatment on the incidence, onset and severity of GVHD. Recipient mice were treated with 60 μg of D-GLAT or PBS daily for the first five weeks after transplant followed by a tapering schedule over an additional four weeks. The dosage of 60 μg/injection was selected based on the prolonged half-life of D-GLAT and was administered intraperitoneally (ip). Treatment was initiated on day −1 and after five weeks the frequency of injections was tapered to three times per week for the following two weeks and to two times per week for another two weeks. Once a week the copolymer D-GLAT was administered with incomplete Freund's adjuvant (IFA) ip as a depot dose. Treatment was discontinued after 9 weeks.

TABLE 1

Effect of treatment with L-GLAT on the induction of GVHD in B10.D2 → Balb/c recipients.
Exp. 1

| Group | n | Incidence day 30 | Incidence day 70 | Incidence day 100 | Incidence day 140 | Mean Onset¶ (days) | Mean Severity¶ | MST (days) | % Actuarial Survival (day) |
|---|---|---|---|---|---|---|---|---|---|
| L-GLAT | 10 | 0/10** | 2/10* | 6/10 | 6/10 | 67.8 | 1.2 | >140 | 90.0 (140)§ |
| HEL | 6 | 6/6 | 6/6 | †† | †† | 20.3 | 6.0 | 40.5 | 16.7 (140) |
| PBS | 10 | 10/10 | 10/10 | †† | †† | 21.3 | 5.4 | 47 | 10.0 (140) |

TABLE 2

Effect of treatment with L-GLAT on the induction of GVHD in B10.D2 → Balb/c recipients.
Exp. 2

| Group | n | Incidence day 30 | Incidence day 70 | Incidence day 100 | Incidence day 140 | Mean Onset¶ (days) | Mean Severity¶ | MST (days) | % Actuarial Survival (day) |
|---|---|---|---|---|---|---|---|---|---|
| L-GLAT | 9 | 1/9¶ | 6/9 | 7/9 | 8/9 | 50.6 | 4.1 | 121 | 33.3 (140) |
| HEL | 4 | 4/4 | †† | †† | †† | 21.8 | 7.0 | 36 | 0 (69) |
| PBS | 9 | 9/9 | 9/9 | †† | †† | 20.2 | 5.2 | 40.5 | 0 (96) |
| TGA | 9 | 9/9 | 9/9 | 9/9 | †† | 19.9 | 4.7 | 63 | 11.1 (140) |

The results are shown in Table 3. D-GLAT treatment reduced the overall incidence of GVHD after allogeneic bone marrow transplantation from 100% (7/7) in control mice to 43% (3/7) in D-GLAT-treated animals on day 30. Two of seven animals treated with D-GLAT did not develop any signs of GVHD beyond the observation period of 140 days after transplant. Furthermore, treatment with D-GLAT improved overall disease severity as gauged by the mean disease severity score (Table 3).

Figure 3:
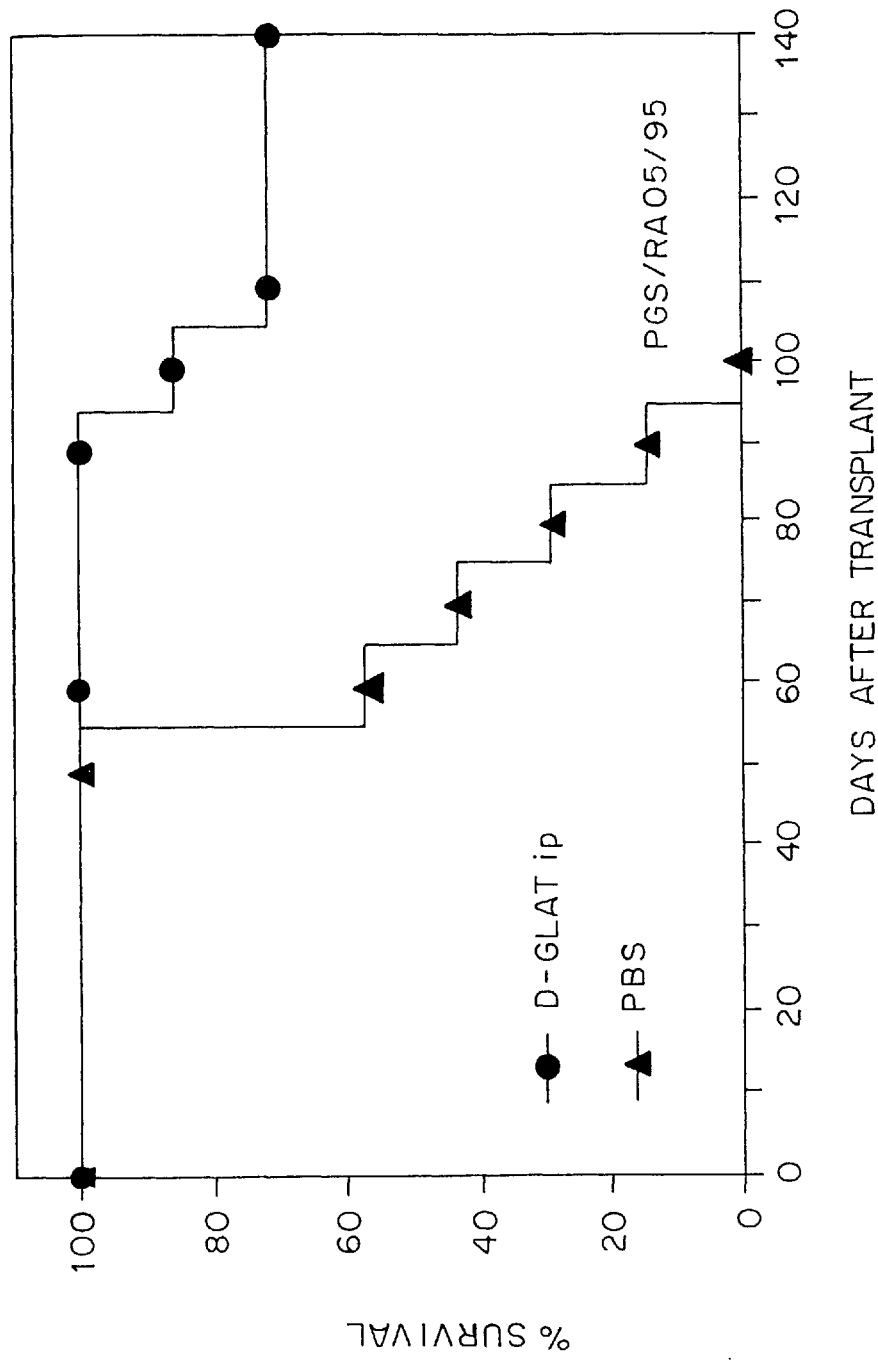
FIG. 3 shows the effect on survival of BALB/c mice transplanted with bone marrow and spleen cells from B10.D2 mice after treatment with D-GLAT or PBS.

(iii) Effect of D-GLAT treatment on survival. Treatment with D-GLAT improved long-term survival from lethal graft-versus-host disease. As shown in FIG. 3, 5/7 (71.4%) of experimental mice survived more than 140 days after transplant as compared to 0/7 of PBS-treated control mice.

TABLE 3

Effect of treatment with D-GLAT on the induction of GVHD in B10.D2 → Balb/c recipients.
Exp. 3

| Group | n | Incidence day 30 | Incidence day 70 | Incidence day 100 | Incidence day 140 | Mean Onset$^I$ (days) | Mean Severity$^{II}$ | MST (days) | % Actuarial Survival (day) |
|---|---|---|---|---|---|---|---|---|---|
| D-GLAT | 7 | 3/7 | 5/7 | 5/7 | 5/7 | 34.8 | 2.1 | >140 | 71.4 (140) |
| PBS | 7 | 7/7 | 7/7 | †† | †† | 21.9 | 5.6 | 60.5 | 0 (96) |

$^I$Means are states as overall means of the respective groups.
$^{II}$GVHD-related mortality. MST: median survival time (in days).

Example 4
Prevention of GVHD in humans (i) Patients

A protocol is established for patients aged 60 years or less and eligible for allogeneic bone marrow transplantation from histocompatible sibling donors for acute non-lymphoblastic leukemia or acute lymphoblastic leukemia not in first remission, chronic myelogenous leukemia not in chronic phase or relapsed patients with non-Hodgkin's lymphoma. Without bone marrow transplantation, these patients have expected survival measured in months. The benefits for these subjects is the use of high dose therapy in curing their disease and the potential prophylaxis against morbidity associated with allogeneic bone marrow transplantation, such as GVHD.

(ii) Conditioning Regimen

Patients are submitted to a conditioning regimen comprising fractionated total body irradiation by administering 120 cGy per fraction 2 to 3 times daily over 4 days (days −8 to −5) to a total dose of 1200 cGy, a multiple drug treatment including, e.g. etoposide (60 mg/kg) over 4 hours at day −4, cyclophosphamide (60 mg/kg) over 1 hour at day −2, antibacterial agents, and standard prophylaxis agents against GVHD, e.g. cyclosporine, methotrexate and prednisone.

(iii) GVHD prophylaxis

GLAT copolymer is administered to the patient subcutaneously (sc), intramuscularly (im) or intravenously (iv) as a twice daily injection a a dosage of 1–500 mg twice daily. The treatment starts at day −2 before and is continued until day +60 after the allogeneic bone marrow transplantation (BMT). This day is chosen since nearly all of the acute GVHD that may occur, will do so by day +40.

Standard prophylaxis against GVHD with cyclosporin and prednisone is also continued. Cyclosporine is administered until the patient is able to sustain oral caloric intake and has no evidence of gastrointestinal toxicity (usually around the end of the first month, 4th week following BMT), at a dose from 1.5 to 5 mg/kg iv twice daily, by infusion in the first 35 days and then orally (per os) until the end of the treatment (day +180). Serum samples are obtained and, if necessary, the drug concentration is adjusted to prevent drug-related toxicities. The aim is for a level of cyclosporine between 200–500 ng/ml. Methylprednisolone is administered iv until patients can be switched to oral (p.o.) prednisone. For example, it is administered iv at a dose of 0.25 mg/kg–0.5 mg/kg from day +7 to +28 and p.o. at a dose of 0.4 mg/kg–0.1 mg/kg until the end of the treatment (day +180).

The first phase of the treatment is to establish engraftment. If engraftment is established, the post-transplantation immunosuppression is then stepwise decreased. The first step is to stop the use of prednisone. If no GVHD occurs, then the use of cyclosporine is stopped (see statistical analysis). At that time only the GLAT coplymer is used as the immunosuppressive regimen.

(iv) Statistical analysis

Current engraftment success rate of bone marrow is close to 100% with a rate of about 50% at 20 days for patients satisfying the eligibility criteria of this protocol. Among these patients, the rate of relapse depends on the disease and remission status. The time to relapse curve is well approximated by an exponential curve over this interval. Both the engraftment rate at 20 days and the relapse rate are monitored statistically as the data become available on other patients treated by the same protocol.

The engraftment rate at 20 days provides the basis for stopping early to avoid putting more patients at risk than necessary if the stem cells take longer to engraft than anticipated. The binary endpoint of success by the 20th day is monitored by sequential test, using 20 as the hypothesized median based on past experience, and using a boundary for inferiority fixed to provide a Type I risk of 5% (one sided) and a degree of conservatism midway between constant p level and the O'Brien-Fleming approach.

As the treatment proceeds, the data on relapse is also monitored, using the time to relapse as the endpoint and including all patients under tretment, whether engraftment is successful at the 20th day or not.

REFERENCES

1. Aharoni R., Teitelbaum D., Sela M. and Arnon R. 1993. Eur. J. Immunol. 23:17–25.

2. Bornstein M. B., et. al. 1990. Clinical trials of Cop 1 in multiple sclerosis, in Handbook of Multiple Sclerosis, ed. Cook S. D. Marcel Dekker, Inc., p.469.

3. Fridkis-Hareli M., Teitelbaum D., Gurevith E., Pecht I., Brautbar C., Kwon Q. T., Brenner T., Arnon R., Sela M. 1994. Direct binding of myelin basic protein and synthetic copolymer 1 to class II major histocompatibility complex molecules on living antigen-presenting cells—specificity and promiscuity. Proc. Natl. Acad. Sci. U.S.A. 91: 4872–76.

4. Jacob C. O., Mykytyn K., Tashman N. 1993. DNA polymorphism in cytokine genes based on length variations in simple-sequence tandem repeats. Immunogenetics. 38: 251.

5. Johnson P. K., et al. 1994. Cop 1 positive results—a phase III trial in relapsing remitting MS. 11 Annual Meeting A.N.A. 1994.

6. Schlegel P. G., Aharoni R., Smilek D. E., Fernandez L. P. McDevitt H. O., Tran N., Vaysburd M. and Chao N. J. 1994. Prevention of Graft-Versus-Host Disease by Peptides Binding to Class II Major Histocompatibility Complex Molecules. Blood 84: 2802–10.

7. Sela M., Arnon R. and Teitelbaum D. 1990. Bull. Inst. Pasteur (Paris) 88: 303–314.

8. Teiltelbaum D., Meshorer A., Hirshfeld T., Arnon R. and Sela M. Suppression of experimental allergic encephalomyelitis by a synthetic polypeptide. 1971. Eur. J. Immunol. 1: 242–48.

9. Teiltelbaum D., Webb C., Meshorer A., Arnon R. and Sela M. 1973. Suppression by several synthetic polypeptides of experimental allergic encephalomyelitis induced in guinea pigs and rabbits with bovine and human basic encephalitogen. Eur J Immunol. 3: 272.

10. Teiltelbaum D., Webb C., Meshorer A., Arnon R., Sela M. 1974a. Suppression of experimental allergic encephalomyelitis in rhesus monkeys by a synthetic basic copolymer. Clin. Immunol. Immunopathol. 3: 256.

11. Teiltelbaum D., Meshorer A. and Arnon R. 1974b. Suppression of experimental allergic encephalomyelitis in baboons by Cop 1. Israel J. Med. Sci. 13: 1038.

12. Teitelbaum D., Aharoni R., Arnon R. and Sela M. 1988. Proc. Natl. Acad. Sci U.S.A 85: 9724–28.

13. Webb C., Teitelbaum D., Herz A., Arnon R. and Sela M. 1976. Immunochemistry 13: 333.

We claim:

1. A method for preventing or treating graft-versus-host disease (GVHD) in a patient about to undergo bone marrow or organ transplantation or suffering from GVHD caused by bone marrow or organ transplantation, which comprises administering to said patient an effective amount of a synthetic random copolymer of average molecular weight 4,000–12,000, herein referred to as GLAT copolymer, said GLAT copolymer consisting of glutamic acid (Glu), lysine (Lys), alanine (Ala) and tyrosine (Tyr) residues in a relative molar ratio of 1.4–2.1 parts of Glu to 3.2–4.2 parts of Lys to 4.0–6.0 parts of Ala to 1.0 part of Tyr.

2. A method according to claim 1, wherein the GLAT copolymer has an average molecular weight of about 5,500–10,000.

3. A method according to claim 1, wherein the GLAT copolymer has an average molecular weight of about 6,000–8,000.

4. A method according to claim 1, wherein all amino acid residues in the copolymer have the L configuration, herein referred to as L-GLAT copolymer.

5. A method according to claim 4, wherein said L-GLAT copolymer has an average molecular weight of about 6,000 and a relative molar ratio of 1.7 parts Glu to 3.8 parts Lys to 4.9 parts Ala to 1.0 Tyr.

6. A method according to claim 4, wherein said L-GLAT copolymer has an average molecular weight of about 8,000 and a relative molar ratio of 1.8 parts Glu to 4.0 parts Lys to 6.0 parts Ala to 1.0 parts Tyr.

7. A method according to claim 1, wherein all amino acid residues in the copolymer have the D configuration, herein referred to as D-GLAT copolymer.

8. A method according to claim 1, wherein some of the amino acid residues of the copolymer have the L configuration and the other amino acid residues have the D configuration, herein referred to as DL-GLAT copolymer.

9. A method according to claim 1, wherein the patient is one about to undergo allogeneic bone marrow transplantation or is suffering from GVHD caused by allogeneic bone marrow transplantation.

10. A method according to claim 1, for prevention of GVHD wherein the GLAT copolymer is administered from day −2 prior to the day of transplantation and for at least 60 days after the day of transplantation.

11. A method according to claim 1, wherein other immunosuppressive drugs are also administered to the patient.

12. A method according to claim 1, wherein the immunosuppressive drugs are selected from the group comprising cyclosporine, methotrexate and prednisone.

13. A method according to claim 1 for the treatment of GVHD, wherein said patient is one suffering from GVHD caused by bone marrow or organ transplantation.

14. A method according to claim 1, wherein said GLAT copolymer is administered as intravenous injection.

15. A method according to claim 1, wherein said GLAT copolymer is administered as intramuscular injection.

16. A method according to claim 1, wherein said GLAT copolymer is administered as subcutaneous injection.

* * * * *